(12) United States Patent
Higuchi

(10) Patent No.: US 8,633,977 B2
(45) Date of Patent: Jan. 21, 2014

(54) ELECTRONIC ENDOSCOPE APPARATUS

(75) Inventor: Mitsuru Higuchi, Saitama (JP)

(73) Assignee: FUJINON Corporation, Saitama-Shi (JP)

( * ) Notice: Subject to any disclaimer, the term of this patent is extended or adjusted under 35 U.S.C. 154(b) by 1779 days.

(21) Appl. No.: 11/699,481

(22) Filed: Jan. 30, 2007

(65) Prior Publication Data
US 2007/0183162 A1 Aug. 9, 2007

(30) Foreign Application Priority Data

Jan. 31, 2006 (JP) ................................. 2006-021847

(51) Int. Cl.
*A61B 1/06* (2006.01)
*B60Q 1/124* (2006.01)

(52) U.S. Cl.
USPC ............................................ 348/70; 362/458

(58) Field of Classification Search
USPC .......................................................... 348/70
See application file for complete search history.

(56) References Cited

U.S. PATENT DOCUMENTS

| | | | |
|---|---|---|---|
| 4,885,634 A | 12/1989 | Yabe | |
| 6,707,485 B1 * | 3/2004 | Higuchi et al. | 348/69 |
| 6,980,231 B1 * | 12/2005 | Ohsawa | 348/188 |
| 7,623,150 B2 * | 11/2009 | Kobayashi | 348/45 |
| 2004/0104999 A1 * | 6/2004 | Okada | 348/65 |

FOREIGN PATENT DOCUMENTS

| | | |
|---|---|---|
| JP | 11-75112 A | 3/1999 |
| JP | 2000-253307 A | 9/2000 |
| JP | 2003-93336 A | 4/2003 |

OTHER PUBLICATIONS

Yoichi Miyake, University of Tokyo Press, pp. 148-153.
Yoichi Miyake, Analysis and Evaluation of Digital Color Image, University of Tokyo Press, pp. 41, pp. 147-153 (2000).
European Communication issued May 29, 2011 in corresponding European patent application No. 07 001 979.9.

* cited by examiner

*Primary Examiner* — Firmin Backer
*Assistant Examiner* — Herman Belcher
(74) *Attorney, Agent, or Firm* — Birch, Stewart, Kolasch & Birch, LLP

(57) ABSTRACT

An electronic endoscope apparatus capable of setting the brightness of a displayed spectroscopic image within a desirable range. The apparatus includes: a light source for irradiating white light on an observation target body; a color imaging device for imaging the observation target image; a first color conversion circuit for converting Y/C signals to RGB three color image signals; a spectroscopic image generation circuit for generating a spectroscopic image from the RGB three color image signals; a second color conversion circuit for converting the RGB three color image signals to Y/C signals; a light amount regulation means for regulating the amount of white light irradiated on the observation target body; and a light amount control circuit for controlling the light amount regulation means based on the luminance information provided by the Y/C signals outputted from the second color conversion circuit.

17 Claims, 5 Drawing Sheets

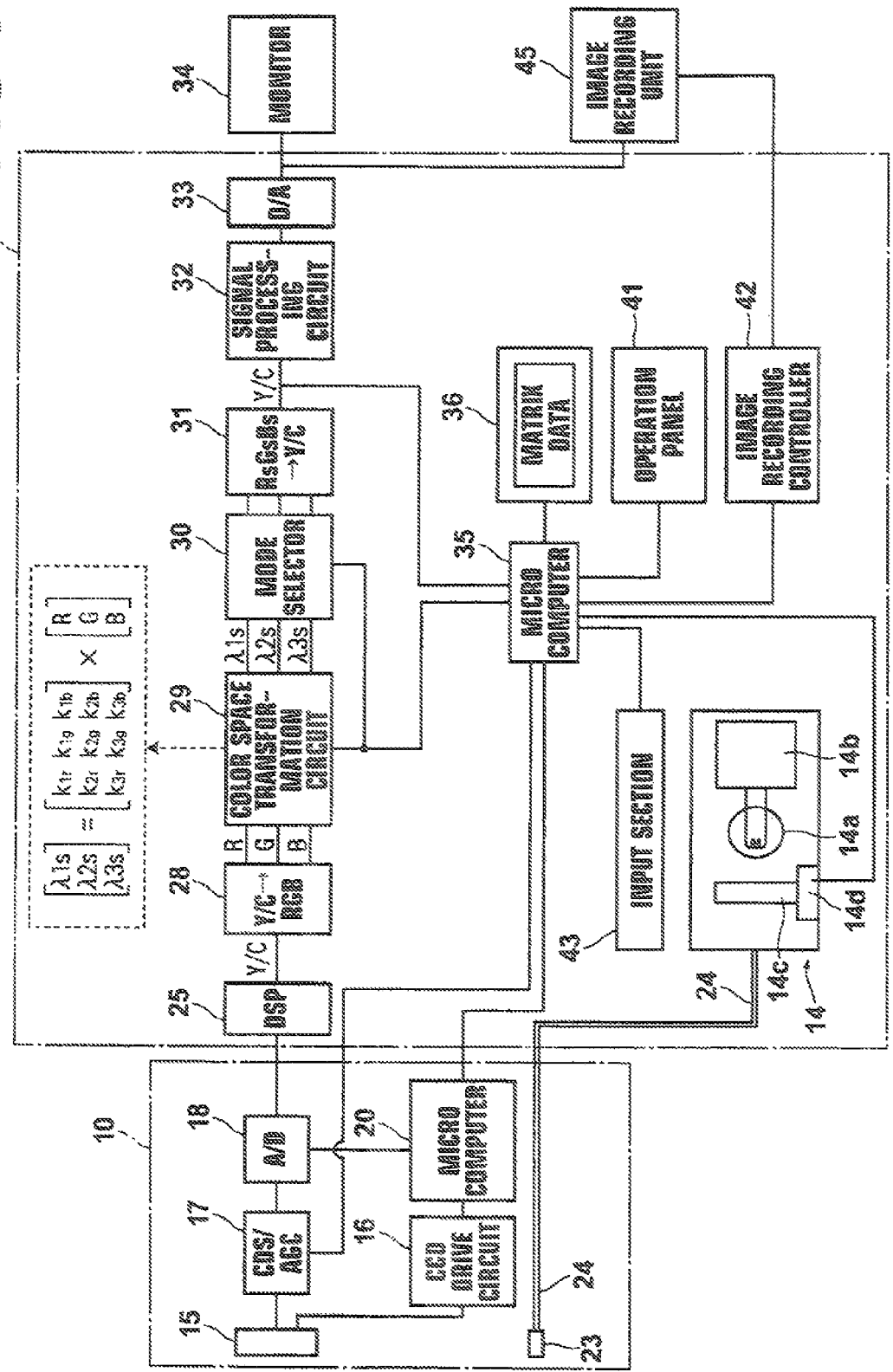

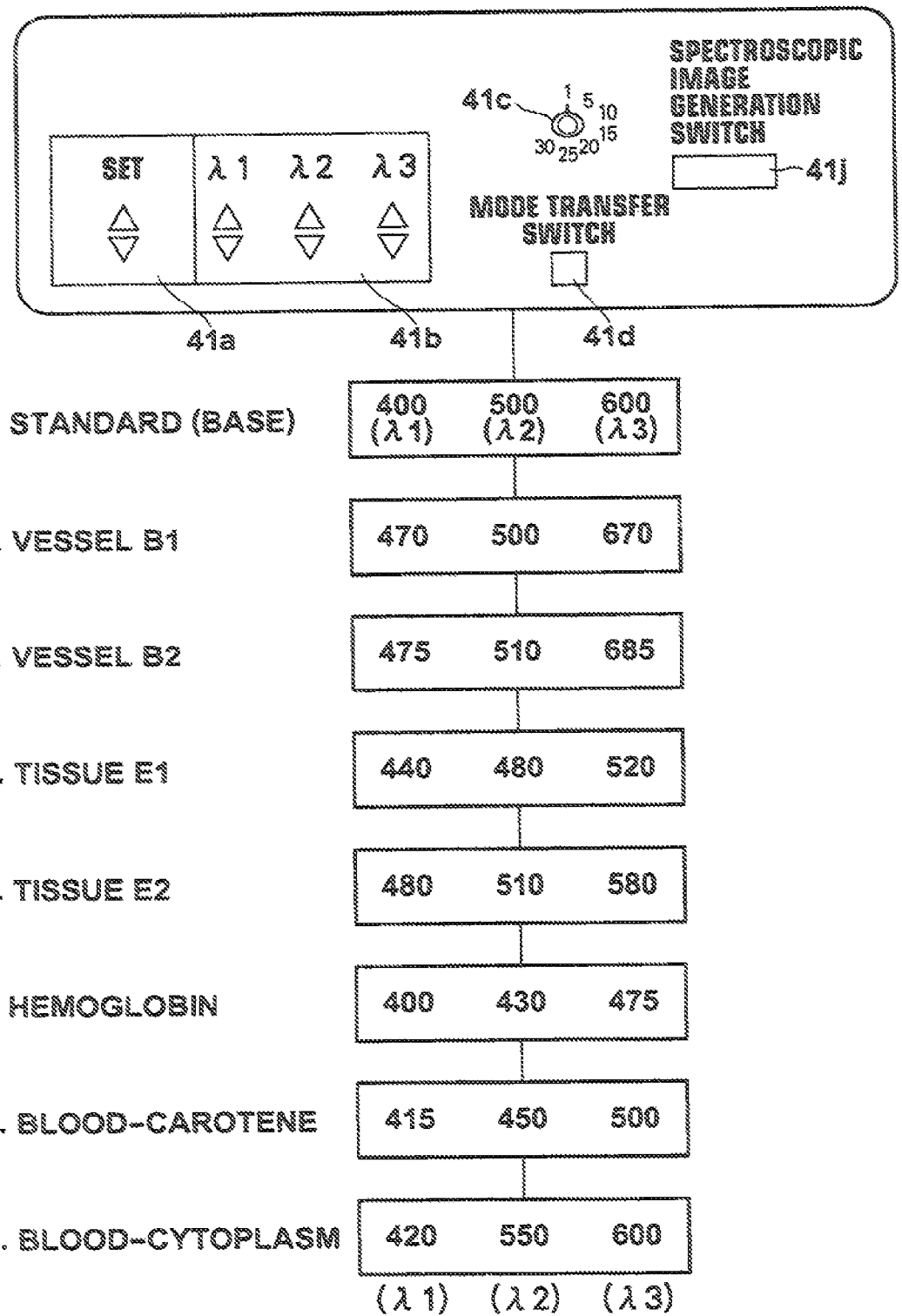

FIG.6

| λ1 | λ2 | λ3 |
|---|---|---|
| 400 | 500 | 600 |
| ↓ | ↓ | ↓ |
| 405 | 510 | 620 |
| ↓ | ↓ | ↓ |
| 410 | 520 | 640 |
| ↓ | ↓ | ↓ |
| 415 | 530 | 660 |
| ↓ | ↓ | ↓ |

FIG.7

(MONOCHROME MODE, SINGLE WAVELENGTH SET)

| λ1 | λ2 | λ3 |
|---|---|---|
| 470 | 470 | 470 |
| ⋮ | ⋮ | ⋮ |
| 500 | 500 | 500 |
| ⋮ | ⋮ | ⋮ |
| 530 | 530 | 530 | ized
ELECTRONIC ENDOSCOPE APPARATUS

CROSS-REFERENCE TO RELATED APPLICATIONS

This application claims foreign priority based on Japanese Patent Application No. 2006-021847 filed on Jan. 31, 2006, the entire contents of this foreign priority application being hereby incorporated by reference.

BACKGROUND OF THE INVENTION

1. Field of the Invention

The present invention relates to an electronic endoscope apparatus, and more specifically to an electronic endoscope apparatus capable of generating and displaying a spectroscopic image (picture) within a specific wavelength range by performing arithmetic operation on the image signals representing a color image.

2. Description of the Related Art

Recently, in the field of electronic endoscope systems with a solid state imaging device, those that performs spectroscopic imaging using combined narrow bandpass filters based on the spectral reflection factors at digestive organs, such as gastric mucosa and the like, i.e., electronic endoscope systems having therein narrow-band filters (Narrow Band Imaging, NBI) have been drawing attention. The system includes three narrow (wavelength) bandpass filters, instead of frame sequential type R (red), G (green), and B (blue) rotation filters. In the system, illumination light beams are sequentially outputted through the narrow bandpass filters, and three signals obtained by the illumination light beams are processed by changing the weighting thereof in the similar manner as in the R, G, B (RGB) signals, thereby a spectroscopic image is generated. According to such spectroscopic images, microscopic structures and the like, which were unable to be obtained in the past, may be detected in digestive organs, such as a stomach and a large intestine.

Unlike the frame sequential type endoscope system that uses narrow bandpass filters described above, the so-called simultaneous type endoscope system uses microscopic mosaic color filters which are disposed on the solid state imaging device. In the simultaneous type endoscope system, a method for generating a spectroscopic image based on the image signals obtained by imaging a observation target body while irradiating white light on the body is proposed as described, for example, in Japanese Unexamined Patent Publication 2003-93336, and a non-patent literature by Yoichi Miyake, University of Tokyo Press, 2000, pp 41, pp 147-153 currently available only in Japanese, and the title of which may be tentatively translated as "Analysis and Evaluation of Digital Color Image"). In the method, relationships between the respective RGB color sensitivity characteristics converted to numerical data, and spectroscopic characteristics of a specific narrow bandpass converted to numeral data are obtained as matrix data (a set of coefficients), and spectroscopic image signals are obtained by estimating a spectroscopic image which would be obtained through narrow bandpass filters by performing arithmetic operation between the matrix data and the RGB signals. Spectroscopic image generation through such arithmetic operation does not require a plurality of different filters corresponding to intended wavelength regions and replacement thereof, so that the system may be kept small with reduced cost.

In the mean time, in electronic endoscope systems, it is customary that the brightness of a displayed image is controlled within a desirable range to facilitate the observation of the image. Generally, such brightness control is performed through controlling the amount of light irradiated on the observation target body from the light source as described, for example, in Japanese Unexamined Patent Publication No. 2000-253307, or through controlling the gain of an amplifier for amplifying image signals outputted from the imaging device as described, for example, in Japanese unexamined Patent Publication No. 11 (1999)-75112. More specifically, as described in the patent publications described above, a method in which the opening of the aperture diaphragm disposed in front of the light source is controlled based on the luminance information (e.g., average luminance value of all of the pixels in a single frame, or the like) provided by the image signals outputted from the imaging device, or a method in which the gain of the amplifier circuit is controlled based also on the luminance information is proposed.

The control for setting the brightness of a displayed image within a predetermined range is, of course, desirable for the electronic endoscope systems for obtaining spectroscopic images described above. Here, in this case also, it may be conceivable to control the amount of light irradiated on the observation target body, or to control the gain of the amplifier circuit for amplifying the image signals outputted from the imaging device based on the luminance information provided by the image signals outputted from the imaging device. Contrary to the expectation, however, it has been found that such control method decreases the brightness of the spectroscopic images.

SUMMARY OF THE INVENTION

The present invention has been developed in view of the circumstances described above, and it is an object of the present invention to provide an electronic endoscope apparatus for obtaining a spectroscopic image capable of accurately setting the brightness of the spectroscopic image at a desirable level.

The first electronic endoscope apparatus of the present invention is an electronic endoscope apparatus comprising:

a light source for irradiating white light on an observation target body;

a color imaging device for imaging the observation target image receiving the white light;

a first color conversion circuit for converting Y (luminance)/C (chrominance difference) signals outputted from the color imaging device to RGB three color image signals;

a spectroscopic image generation circuit for generating a spectroscopic image within a predetermined wavelength range from the RGB three color image signals;

a second color conversion circuit for converting the RGB three color image signals representing the spectroscopic image to Y/C signals;

a light amount regulation means for regulating the amount of white light irradiated on the observation target body from the light source; and a light amount control circuit for controlling the light amount regulation means based on the luminance information provided by the Y/C signals outputted from the second color conversion circuit to set the brightness of the spectroscopic image within a predetermined range.

As for the light amount regulation means, a light amount regulation means that combines an aperture diaphragm disposed on the front side of the light source, i.e., on the side of the observation target body with a means for regulating the opening of the aperture diaphragm, a means that regulates the amount of light emitted from the light source by changing the drive current or drive voltage thereof, or the like are preferably used.

The second electronic endoscope apparatus of the present invention is an electronic endoscope apparatus comprising:

a light source for irradiating white light on an observation target body;

a color imaging device for imaging the observation target image receiving the white light;

a first color conversion circuit for converting Y (luminance)/C (chrominance difference) signals outputted from the color imaging device to RGB three color image signals;

a spectroscopic image generation circuit for generating a spectroscopic image within a predetermined wavelength range from the RGB three color image signals;

a second color conversion circuit for converting the RGB three color image signals representing the spectroscopic image to Y/C signals;

an amplifier circuit for gain adjustably amplifying the Y/C signals outputted from the color imaging device; and a gain control circuit for controlling the gain of the amplifier circuit based on the luminance information provided by the Y/C signals outputted from the second color conversion circuit to set the brightness of the spectroscopic image within a predetermined range.

The second electronic endoscope apparatus of the present invention may further includes the light amount regulation means and the light amount control circuit included in the first electronic endoscope apparatus. In this case, for example, it is preferable that a configuration be adopted in which either the light amount regulation by the light amount regulation means or the gain adjustment of the amplifier circuit is normally performed, and in case that desirable brightness of a spectroscopic image is not obtained by either one of the adjustments, the other is performed additionally.

The study conducted by the inventor of the present invention has revealed the following cause of the problem that the brightness of a spectroscopic image is decreased when the method described in Japanese Unexamined Patent Publication No. 2000-253307 or 11 (1999)-75112 is applied to an electronic endoscope apparatus for obtaining a spectroscope image.

That is, when Y/C signals outputted from the color imaging device are converted to RGB three color image signals, and a spectroscope image within a predetermined wavelength range is generated from the RGB three color image signals, image signals of narrow wavelength regions are extracted from the color image signal representing image information of a broad wavelength range, and used for the generation of the spectroscope image. Thus, the brightness of the spectroscopic image is decreased by the amount corresponding to the amount of image signals not used in the spectroscopic image generation. As such, if control for setting the brightness of a spectroscopic image to an optimum value is performed based on the luminance information provided by the Y/C signals before converted to RGB three color image signals, the brightness of the actually generated image becomes lower than the brightness of the optimum value.

Based on the new knowledge, in the first electronic endoscope apparatus of the present invention, the light amount regulation means is regulated based on the luminance information provided by the Y/C signals outputted from the second color conversion circuit, i.e., the Y/C signals representing a spectroscopic image, instead of the luminance information provided by the Y/C signals before being served to the generation of the spectroscopic image. This allows the brightness of the actually generated spectroscopic image to be set at an optimum value.

Also, in the second electronic endoscope apparatus of the present invention, the gain of the amplifier circuit is controlled based on the luminance information provided by the Y/C signals outputted from the second color conversion circuit, i.e., the Y/C signals representing a spectroscopic image, instead of the luminance information provided by the Y/C signals before being converted to the RGB three color image, and the level of the Y/C signals outputted from the second color conversion circuit is set within a target range.

Thus, in this case also, the brightness of the actually generated spectroscopic image may be set at an optimum value.

BRIEF DESCRIPTION OF THE DRAWINGS

FIG. 1 is a block diagram of the electronic endoscope apparatus according to an embodiment of the present invention, illustrating the construction thereof.

FIG. 2 is a drawing illustrating a layout of the operation panel and an example set of wavelengths of a processor apparatus included in the electronic endoscope apparatus shown in FIG. 1.

FIG. 6 is a drawing illustrating wavelength alteration implemented by the wavelength alteration switch on the electronic endoscope apparatus shown in FIG. 1.

FIG. 7 is a drawing illustrating a set of wavelengths selected in monochrome mode.

DESCRIPTION OF THE PREFERRED EMBODIMENTS

Figure 3A:
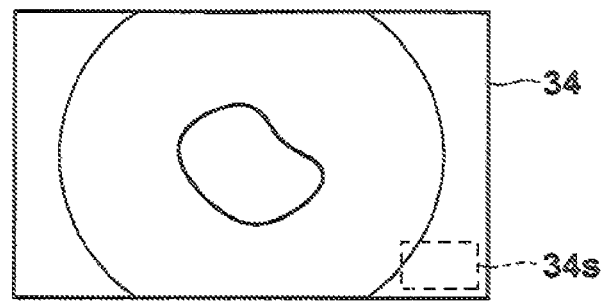
FIGS. 3A to 3C are drawings illustrating the wavelength information display area and an example display on the monitor of the electronic endoscope apparatus shown in FIG. 1.

Hereinafter, exemplary embodiments of the present invention will be described in detail with reference to accompanying drawings. FIG. 1 illustrates a basic construction of the electronic endoscope apparatus according to an embodiment of the present invention. As show in the drawing, the electronic endoscope apparatus includes: a scope 10, i.e., the main body section, and a processor unit 12 to which the scope 10 is detachable attached. The processor unit 12 has therein a light source unit 14 that emits white light. An illumination window 23 is provided at the distal end of the scope 10, and one end of a light guide 24, the other end of which is connected to the light source unit 14, is disposed opposite to the window 23.

The light source unit 14 includes: a lamp 14a that emits white light; a lamp activation circuit 14b that activates the lamp 14a; an aperture diaphragm 14c disposed on the front side of the lamp 14a; and an aperture diaphragm drive section 14d for opening/closing the aperture diaphragm 14c. Note that an optical system for inputting white light emitted from the lamp 14a to the light guide 24 is disposed between the lamp 14a and the light guide 24, but it is omitted in the drawing for clarity. Further, this type of light source unit may be provided separately.

A CCD 15, which is a solid state imaging device, is provided at the distal end of the scope 10. As for the CCD 15, a complementary color CCD having color filters of, for example, Mg (magenta), Ye (yellow), Cy (cyan), and G (green), or a primary color CCD having RGB color filters on the imaging surface may be used.

The CCD 15 is connected to a CCD drive circuit 16 that generates the drive pulse based on a synchronization signal, and to a CDS/AGC (correlated double sampling/automatic gain control) circuit 17 that samples and amplifies image (picture) signals outputted from the CCD 15. An A/D converter 18 is connected to the CDS/AGC circuit 17, which converts analog signals outputted from the CDS/AGC circuit 17 to digital signals. Further, a microcomputer 20 is provided within the scope 10, which controls various circuits provided in the scope 10, as well as performing communication control with the processor unit 12.

In the mean time, the processor unit 12 includes a DSP (digital signal processor) 25. The DSP 25 generates and outputs Y/C signals including a luminance (Y) signal and a chrominance difference signal [C (R−Y, B−Y)] from the output signal of the CCD 15, and a first color conversion circuit 28 is connected thereto. The first color conversion circuit 28 converts the Y/C signals outputted from the DSP 25 to three color image signals of R, G, and B. Note that the DSP may be provided on the side of the scope 10.

The following circuits are connected to the subsequent stage side of the first color conversion circuit 28 in the order described below: a color space transformation circuit 29 for performing matrix operation and outputting image signals representing a spectroscopic image formed of selected wavelength regions $\lambda 1$, $\lambda 2$, and $\lambda 3$; a mode selector 30 for selecting either a monochrome mode in which a spectroscopic image formed of a single narrow wavelength range is generated, or a three color mode in which a spectroscopic image formed of three wavelength regions is generated; a second color conversion circuit 31 for converting image signals of a single wavelength region, or image signals $\lambda 1s$, $\lambda 2s$, and $\lambda 3s$ of three different wavelength regions inputted as Rs, Gs, and Bs signals to Y/C signals; a signal processing circuit 32 for performing other signal processing including mirror image processing, mask generation, character generation and the like; and a D/A converter 33. The D/A converter 33, which is the last stage of these circuits, is connected to a monitor 34, which is, for example, a liquid crystal display, a CRT display or the like, and to an image recording unit 45, such as an optical beam scanning type recording device, or the like. Note that a two color mode in which a spectroscopic image formed of two different wavelength regions may be set, instead of the three color mode to be selected by the mode selector 30.

The processor unit 12 further includes a microcomputer 35 which has functions of communicating with the scope 10, controlling various circuits within the processor unit 12, inputting matrix (coefficient) data for generating a spectroscopic image to the color space transformation circuit 29, and the like. The matrix data for generating a spectroscopic image based on RGB signals are stored in a memory 36 in the form of a table. An example of the matrix data stored in the memory 36 in the present embodiment is like that shown in Table 1 below.

TABLE 1

| Parameter | $K_{pr}$ | $K_{pg}$ | $K_{pb}$ |
|---|---|---|---|
| p1 | 0.000083 | −0.00188 | 0.003592 |
| . | . | . | . |
| . | . | . | . |
| . | . | . | . |

TABLE 1-continued

| Parameter | $K_{pr}$ | $K_{pg}$ | $K_{pb}$ |
|---|---|---|---|
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| . | . | . | . |
| . | . | . | . |
| . | . | . | . |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −0.000036 |
| p51 | 0.005152 | −0.00192 | 0.000088 |
| p52 | 0.005215 | −0.00207 | 0.000217 |
| . | . | . | . |
| . | . | . | . |
| . | . | . | . |
| p61 | 0.00548 | −0.00229 | 0.00453 |
| P1 | 1.00000 | 0.00000 | 0.00000 |
| P2 | 0.00000 | 1.00000 | 0.00000 |
| P3 | 0.00000 | 0.00000 | 1.00000 |

The matrix data in Table 1 includes 61 wavelength region parameters (set of coefficients) p1 to p61 obtained by dividing, for example, the wavelength range of 400 to 700 nm into segments with a bandwidth of 5 nm each, and parameters P1 to P3 for generating an ordinary image. Each of the parameters p1 to p61 includes the coefficients of $k_{pr}$, $k_{pg}$, and $k_{pb}$ (p=1 to 61) to be used for matrix operation. The parameter P1 includes the coefficients (1.00000, 0.00000, and 0.00000), the parameter P2 includes the coefficients (0.00000, 1.00000, and 0.00000), and the parameter P3 includes the coefficients (0.00000, 0.00000, and 1.00000).

In the color space transformation circuit 29, matrix operation of Formula (1) shown below is performed between the coefficients of, $k_{pr}$, $k_{pg}$, and $k_{pb}$, and RGB signals outputted from the first color conversion circuit 28, thereby spectroscopic image signals $\lambda 1s$, $\lambda 2s$, and $\lambda 3s$ are generated.

$$\begin{bmatrix} \lambda 1 \\ \lambda 2 \\ \lambda 3 \end{bmatrix} = \begin{bmatrix} k_{1r} & k_{1g} & k_{1b} \\ k_{2r} & k_{2g} & k_{2b} \\ k_{3r} & k_{3g} & k_{3b} \end{bmatrix} \times \begin{bmatrix} R \\ B \\ G \end{bmatrix}$$

That is, when, for example, 500 nm, 620 nm, and 650 nm are selected respectively as the wavelength regions $\lambda 1$, $\lambda 2$, and $\lambda 3$ forming a spectroscopic image, the matrix operation is performed using the coefficients (−0.00119, 0.002346, and 0.0016) of parameter p21 corresponding to the center wavelength of 500 nm, coefficients (0.004022, 0.000068, and −0.00097) of parameter p45 corresponding to the center wavelength of 620 nm, and coefficients (0.005152, −0.00192, and 0.000088) of parameter p51 corresponding to the center wavelength of 650 nm as the coefficients ($k_{pr}$, $k_{pg}$, and $k_{pb}$).

When an instruction for displaying or recording an ordinary image is given in the manner to be described later, the color space transformation circuit 29 performs the matrix operation described above using the coefficients of parameters P1 to P3. Accordingly, in this case, the RGB signals outputted from the first color conversion circuit 28 are outputted as they are from the color space transformation circuit 29.

An operation panel 41, an image recording controller 42, and an input section 43 including a keyboard and the like are connected to the microcomputer 35, in addition to the memory 36. FIG. 2 illustrates the operation panel 41 in detail. The operation panel 41 includes: a set selection switch 41a for selecting, for example, one of the wavelength sets of (a) to (h), which are also schematically shown in FIG. 2; wavelength selection switches 41b for selecting the center wavelengths of the wavelength regions λ1, λ2, and λ3; an alteration width setting switch 41c for setting the width of the wavelength alteration implemented by the wavelength selection switches 41b; a mode transfer switch 41d for transferring between a monochrome mode, in which a single wavelength is selected, and a three color mode; and a spectroscopic image generation switch 41j for instructing the generation of a spectroscopic image. Note that the spectroscopic image generation switch 41j may be provided on the side of the scope 10.

Operation of the electronic endoscope apparatus constructed in the manner as described above will now be described. First, generation of an ordinary image and a spectroscopic image will be described. When generating these images, the light source unit 14 shown in FIG. 1 is activated, and white light emitted therefrom is inputted to the light guide 24 through the aperture diaphragm 14c, which is then outputted from the distal end of the light guide 24 disposed within the scope 10 and irradiated on an observation target body. Then, the observation target body is imaged by the CCD 15 driven by the CCD drive circuit 16, and the obtained image signals are outputted therefrom. The image signals are subjected to the correlated double sampling and automatic gain control amplification in the CDS/AGC circuit 17, which are then A/D converted in the A/D converter 18 and inputted to the DSP 25 of the processor unit 12 as digital signals. The automatic gain control of the CDS/AGC circuit 17 will be described in detail later.

In the DSP 25, gamma processing is performed on the output signal of the scope 10, and color conversion is performed on the signals obtained through the color filters of Mg, Ye, Cy, and G, thereby Y/C signals are generated in the manner as described above. The Y/C signals outputted from the DSP 25 are inputted to the first color conversion circuit 28, where they are converted to RGB signals. The RGB signals are supplied to the color space transformation circuit 29, where matrix operation is performed between the RGB signals and matrix data for generating a spectroscopic image.

Now, the matrix operation will be described in detail. When the spectroscopic image generation switch 41j on the operation panel 41 shown in FIG. 2 is depressed, the matrix operation of Formula (1) described above is performed for generating a spectroscopic image by the color space transformation circuit 29 using the matrix data stored in the memory 36 and the RGB signals. That is, in this case, three wavelength regions of λ1, λ2, and λ3 are set through the operation panel 41, and the matrix data corresponding to the three wavelength regions are read out from the memory 36 and inputted to the color space transformation circuit 29 by the microcomputer 35.

If, for example, wavelengths of 500, 620, and 650 nm are selected as the three wavelength regions of λ1, λ2, and λ3, the coefficients of parameters p21, p45, and p51 in Table 1, each corresponding to each wavelength, are used, and spectroscopic image signals λ1s, λ2s, and λ3s are generated from the RGB signals through the matrix operation of Formula (2) shown below.

$$\begin{bmatrix} \lambda 1s \\ \lambda 2s \\ \lambda 3s \end{bmatrix} = \begin{bmatrix} -0.00119 & 0.002346 & 0.0016 \\ 0.004022 & 0.000068 & -0.00097 \\ 0.005152 & -0.00192 & 0.000088 \end{bmatrix} \times \begin{bmatrix} R \\ B \\ G \end{bmatrix}$$

If the three color mode is selected by the mode selector 30, the spectroscopic image signals λ1s, λ2s, and λ3s are inputted to the second color conversion circuit 31 as the three color image signals Rs, Gs, and Bs respectively. If the monochrome mode is selected, anyone of the spectroscopic image signals λ1s, λ2s, and λ3s is inputted to the second color conversion circuit 31 as the Rs, Gs, or Bs signal. In the second color conversion circuit 31, the three color image signals Rs, Gs, and Bs are converted to Y/C signals (Y, Rs−Y, Bs−Y), and the Y/C signals are inputted to the monitor or the image recording unit 45 through the signal processing circuit 32 and the D/A converter 33.

Figure 4:
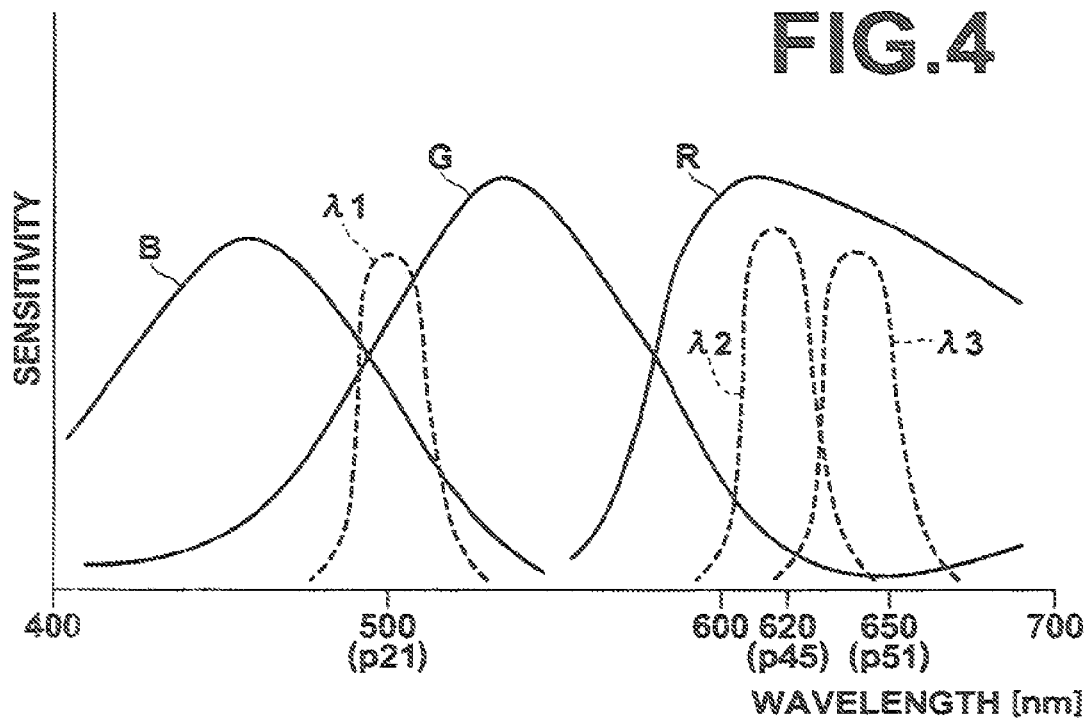
FIG. 4 is a graph illustrating an example wavelength range of a spectroscopic image together with the spectroscopic sensitivity characteristics of a primary color CCD.
Figure 5:
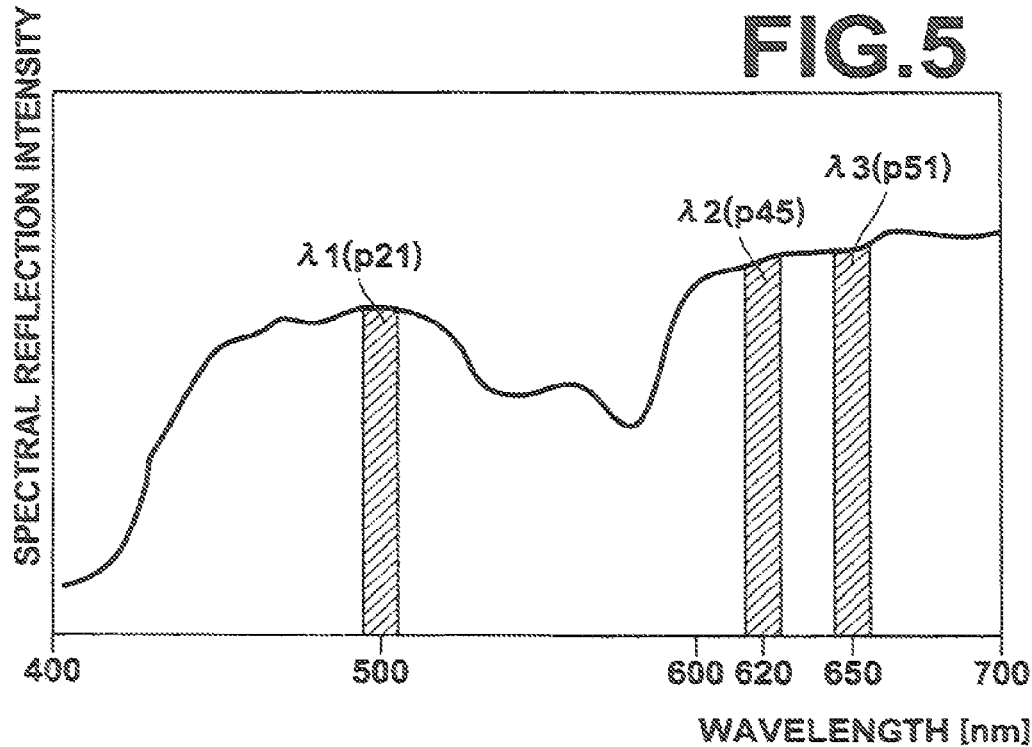
FIG. 5 is a graph illustrating an example wavelength range of a spectroscopic image together with a reflectance spectrum of a living body

The spectroscopic image displayed on the monitor 34 based on the Y/C signals includes color components in the wavelength range shown in FIGS. 4 and 5. That is, FIG. 4 is a conceptual diagram in which the three wavelength regions λ1, λ2, and λ3 are superimposed on the spectroscopic sensitivity characteristics R, G, and B of the color filters of a primary color CCD 15. FIG. 5 is a conceptual diagram in which the three wavelength regions λ1, λ2, and λ3 are superimposed on the reflectance spectrum of a living body. The spectroscopic image signals λ1s, λ2s, and λ3s generated by the example parameters p21, p45, and p51 are color signals within a wavelength regions of approximately ±10 nm centered on 500, 620, and 650 nm respectively as shown in FIG. 5, so that a spectroscopic image (moving picture or still image) formed of color combinations in these three wavelength regions.

Next, selection of the wavelength regions λ1, λ2, and λ3 will be described. In the present embodiment, the following eight wavelength sets are stored in an area of the memory 36 shown in FIG. 1 as the default wavelength sets of λ1, λ2, and λ3 as shown in FIG. 2. Namely, a standard set (a), for example, of 400, 500, and 600 (nm, the same applies hereinafter); a vessel B1 set (b) of 470, 500, and 670 for visualizing a vessel; a vessel B2 set (c) of 475, 510, and 685 for also visualizing a vessel; a tissue E1 set (d) of 440, 480, and 520 for visualizing a specific tissue; a tissue E2 set (e) of 480, 510, and 580 for also visualizing a specific tissue; a hemoglobin set (f) of 400, 430, and 475 for visualizing the difference between oxyhemoglobin and deoxyhemoglobin; a blood-carotene set (g) of 415, 450, and 500 for visualizing the difference between blood and carotene; and a blood-cytoplasm set (h) of 420, 550, and 600 for visualizing the difference between blood and cytoplasm.

When the electronic endoscope apparatus is initially started up by supplying power after factory shipment, the default wavelength sets described above are selected by the microcomputer 35. Then, if the spectroscopic image generation switch 41j on the operation panel 41 shown in FIG. 2 is depressed, the standard set (a) among the selected wavelength sets is displayed on a wavelength information display area 34s of the monitor 34 shown in FIG. 3A. Here, if the mode transfer switch 41d is depressed and the three color mode is selected, the parameters corresponding to λ1=400, λ2=500, and λ3=600 of the standard set (1) are read out from the memory 36, and inputted to the color space transformation circuit 29. The color space transformation circuit 29 performs the matrix operation described above using the inputted parameters and generates spectroscopic image signals λ1s, λ2s, and λ3s. Then, a spectroscopic image based on the spectroscopic image signals λ1s, λ2s, and λ3s is displayed on the monitor 34 shown in FIG. 3A.

Further, the operator of the apparatus, such as a clinician or the like, may freely select other wavelength sets (b) to (h) of the default wavelength sets by operating the set selection switch 41a on the operation panel 41 shown in FIG. 2. Then, the selected wavelength set is displayed on the wavelength information display area 34s of the monitor 34 shown in FIG. 3A by the microcomputer 35. At the same time, in this case also, parameters corresponding to λ1, λ2, and λ3 of the selected wavelength set are read out from the memory 36 by the microcomputer 35 and inputted to the color space transformation circuit 29. The color space transformation circuit 29 performs the matrix operation described above using the inputted parameters and generates spectroscopic image signals λ1s, λ2s, and λ3s. Then, the spectroscopic image based on the spectroscopic image signals λ1s, λ2s, and λ3s is displayed on the monitor 34 shown in FIG. 3A.

As shown in FIG. 2, the set selection switch 41a includes an upward switch having an upward triangular section, and a downward switch having a downward triangular section. Every time the former is depressed, the wavelength sets are sequentially selected in the order of (a), (h), (g) - - -, and every time the latter is depressed, the wavelength sets are sequentially selected in the order of (a), (b), (c) - - - .

Further, while one of the wavelength set (a) to (h) is selected, each of the wavelength regions λ1, λ2, and λ3 may be changed freely by the operator by operating the corresponding wavelength selection switch 41b. When changing the wavelength regions, the wavelength alteration width may be changed by the alteration width setting switch 41c. That is, by rotating the knob of the alteration width setting switch 41c, a continuous alteration or a stepwise alteration may be set, like a virtually continuous alteration of 1 nm width, or a stepwise alteration of 5, 10, or 20 nm. Note that when the wavelength is altered, for example, in 1 nm width, 301 wavelength regions are set within the range of 400 to 700 nm, and matrix data corresponding to the 301 wavelength regions (p'1 to p'301) are created.

FIG. 6 illustrates the selection of the wavelength regions. If the 5 nm width is selected, the wavelength is changed like from 400 to 405, and then to 410 as indicated in the alteration of λ1, and if the 10 nm width is selected, it is changed like from 600 to 620, and then to 640 as indicated in the alteration of λ3, and these values are displayed on the wavelength information display area 34s of the monitor 34.

Figure 3B:
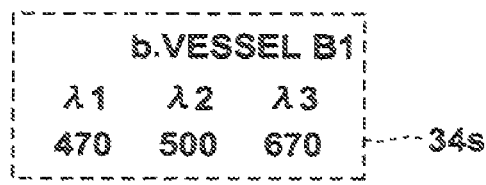
Figure 3C:
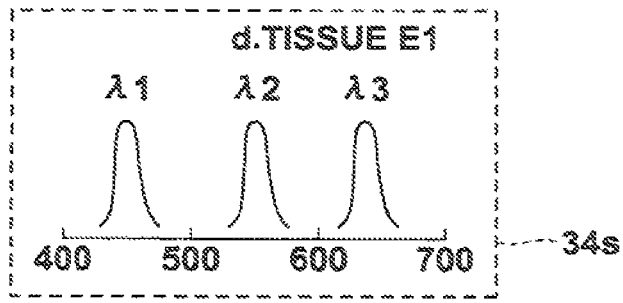

FIG. 3B illustrates in detail an example display status of the wavelength information display area 34s. In the present embodiment, the wavelength information is displayed on the wavelength information display area 34s provided at the bottom right section or the like of the monitor 34, as shown in FIG. 3A, through character generation or the like in the signal processing circuit 32. That is, values of selected wavelength (nm) are displayed under the characters of λ1, λ2, and λ3 on the wavelength information display area 34s, as shown in FIG. 3B. Alternatively, as shown in FIG. 3c, the selected wavelength regions may be visualized by a movable graph with the horizontal axis as the wavelength and the vertical axis as the sensitivity (which corresponds to the graph shown in FIG. 4).

The mode transfer switch 41d shown in FIG. 2 is used to perform transfer between the monochrome mode and the three color mode. When the apparatus is operated in the three color mode, if the mode transfer switch 41d is depressed, the apparatus is transferred to the monochrome mode, and all of the wavelength regions λ1, λ2, and λ3 are set to a same value, like 470, 470, and 470. Then, a common wavelength region is displayed on the monitor 34 as shown in FIG. 7. Note that any value may be selected for the common wavelength region by the wavelength selection switches 41b.

Here, in addition to eight default wavelength sets described above, other wavelength sets may be provided in response to requests from the doctors, the users of the apparatus, and stored in the memory for use as appropriate. Further, some or all of the functions of the switches on the operation panel 41 may be replaced by the key functions of the keyboard.

While the a spectroscopic image is generated and displayed in the manner as described above, if the spectroscopic image generation switch 41j on the operation switch 41 shown in FIG. 2 is depressed again, or if the spectroscopic image generation switch 41j is not depressed from the start, the coefficients of the parameters P1 to P3 described above are selected as the coefficients of the matrix operation in the color space transformation circuit 29, and thereby the RGB signals outputted from the first color conversion circuit 28 are outputted as they are from the color space transformation circuit 29. Then, the RGB signals are converted to Y/C signals in the second color conversion circuit 31, and the Y/C signals are inputted to the monitor 34 through the signal processing circuit 32 and the D/A converter 33. Therefore, an ordinary color image (moving picture or still image) of the observation target image is displayed on the monitor 34.

In the present embodiment, the output of the D/A converter is connected to the image recording unit 45 as well as to the monitor 34. Thus, if an image recording instruction is given to the image recording unit 45 from the image recording controller 42, which is controlled by the microcomputer 35, a hard copy of an ordinary color image or a spectroscopic image of a scene specified by the image recording instruction is outputted from the image recording unit 45.

A method for setting the brightness of an ordinary color image or a spectroscopic image displayed on the monitor 34, or of a hardcopy thereof outputted from the image recording unit 45 within a desirable range will now be described. As shown in FIG. 1, Y/C signals outputted from the second color conversion circuit 31 are also inputted to the microcomputer 35 acting as a light amount control circuit. The microcomputer 35 obtains, for example, an average value of Y (luminance) signals with respect to a single filed of an ordinary color image or a spectroscopic image from the inputted Y/C signals, which is then compared to a predetermined target value, and the aperture diaphragm drive section 14d of the light source unit 14 is controlled based on the comparison results. That is, feedback control is performed such that, if the average value is less than the predetermined target value, the opening of the aperture diaphragm 14c is increased by a predetermined amount, while if it is greater than or equal to the predetermined value, the opening of the aperture diaphragm 14c is decreased by a predetermined amount. The control of the opening of the aperture diaphragm 14c in the manner as described above causes the amount of white light irradiated on the observation target body to be increased or decreased, thereby the brightness of the ordinary image or the spectroscopic image of the observation target body displayed on the monitor 34, or the brightness of the hardcopy thereof outputted from the image recording unit 45 is maintained within a predetermined range.

If light amount control like that described above is performed based on the Y/C signals before inputted to the color space transformation circuit 29, i.e., Y/C signals outputted from the DSP 25, the amount of loss in the signal level due to color space transformation would not be reflected in the light amount control as described earlier. Therefore, the brightness of the displayed image or the hardcopy described above would be reduced. In the present embodiment, such disadvantage may be avoided.

Further, in the present embodiment, if the average value of Y signals described above is less than the target value even the opening of the aperture diaphragm is fully opened, the gain of the CDS/AGC circuit 17 is increased by a predetermined amount by the microcomputer 35. In this way, in case that the brightness of the displayed image or the brightness of the hardcopy thereof is unable to be set within a predetermined range solely by the control of the aperture diaphragm 14c, the brightness may be set within the predetermined range through feedback gain control of the CDS/AGC circuit 17 based on the Y signals. In this case, the CDS/AGC circuit 17 may be directly controlled by the microcomputer 34, or through the microcomputer 20 in the scope 10, in which the microcomputer 20 is controlled by the microcomputer 34.

The combined light amount control through the opening control of the aperture diaphragm 14c and the gain control of the CDS/AGC as in the present embodiment is not necessarily required, and a configuration may be adopted in which only either of them is performed. Further, the light intensity may also be controlled, for example, through control of the drive current or voltage of the lamp 14a by the lamp activation circuit 14b, other than through the control of the opening of the aperture diaphragm 14c.

Further, in the embodiment described above, the light amount control and the gain control are performed based on the average value of Y signals with respect to a single field of an ordinary color image or a spectroscopic image. But the control basis is not limited to such average value, and the light amount control and the gain control may be performed based on a maximum value of Y signals within a single field, or an average value or a maximum value of Y signals within a specific portion of the single field.

The brightness of a spectroscopic image may also be changed by what is known as electronic shutter control in which the charge storage time of the CCD 15, which is determined by the CCD drive circuit 16, is controlled. Thus, the brightness of a spectroscopic image may also be set to a desirable value through the electronic shutter control based on a maximum value of Y signals within a single field, or an average or a maximum value of Y signals within a specific portion of the single field.

Further, in the embodiment described above, the wavelength range of 400 to 700 nm is divided into 61 selectable wavelength regions. If a wavelength set is selected as the wavelength regions λ1, λ2, and λ3 from a wavelength range including the infrared region or only from the infrared region, a spectroscopic image which is similar to an image obtainable through the irradiation of infrared light in the past may be obtained without using a visible light cut filter. Further, in a conventional endoscope apparatus, fluorescence emitted from a cancer tissue or the like by the irradiation of excitation light thereon is imaged. If a wavelength set corresponding to the fluorescent wavelengths is selected as the wavelength set of λ1, λ2, and λ3, a spectroscopic image of a portion emitting the fluorescence may be generated. This has an advantage that an excitation light cut filter is not required.

Still further, in a conventional endoscope apparatus, a pigment such as Indigo, Pyoktanin, or the like is dispersed on an observation target body, and a tissue colored by the pigment dispersal is imaged. If wavelength regions that may visualize a tissue, which may be colored by the dispersal of a pigment, as the wavelength set of λ1, λ2, and λ3, a spectroscopic image which is equivalent to an image obtained by dispersing the pigment may be obtained without requiring the pigment dispersal.

What is claimed is:

1. An electronic endoscope apparatus, comprising:
   a light source for irradiating white light on an observation target body;
   a color imaging device for imaging the observation target image receiving the white light;
   a first color conversion circuit for converting Y (luminance)/C (chrominance difference) signals outputted from the color imaging device to RGB three color image signals;
   a spectroscopic image generation circuit for generating, from the RGB three color image signals, a spectroscopic image within a predetermined wavelength range, said spectroscopic image generation circuit performing a matrix operation using matrix data and the RGB three color image signals to generate the spectroscopic image which is described by spectroscopic three color image signals, and
   wherein
   said predetermined wavelength range is selected to visualize an anatomical characteristic of the observation target body, and
   said predetermined wavelength range is a wavelength range which is narrower than the wavelength range of the observation target image imaged by the color imaging device, and
   said matrix data comprises matrix parameters which correspond to said predetermined wavelength range;
   a second color conversion circuit for converting the spectroscopic three color image signals representing the spectroscopic image to Y/C signals;
   a light amount regulation unit for regulating the amount of white light irradiated on the observation target body from the light source; and
   a light amount control circuit for controlling the light amount regulation unit based on the luminance information provided by the Y/C signals outputted from the second color conversion circuit to set the brightness of the spectroscopic image described by the spectroscopic three color image signals, within a predetermined brightness range, for visualizing the spectroscopic image.

2. The electronic endoscope apparatus according to claim 1, wherein the light amount regulation unit comprises an aperture diaphragm disposed in the light path of the white light, and an aperture diaphragm drive section for regulating the opening of the aperture diaphragm.

3. The electronic endoscope apparatus according to claim 1, wherein the light amount regulation unit comprises a unit for controlling the drive current or drive voltage of the light source.

4. The electronic endoscope apparatus according to claim 1, wherein the light amount control circuit uses an average value of Y signals with respect to a single field of an image or a specific portion of the field as the luminance information.

5. The electronic endoscope apparatus according to claim 1, wherein the light amount control circuit uses a maximum value of Y signals with respect to a single field of an image or a specific portion of the field as the luminance information.

6. The electronic endoscope apparatus according to claim 1, wherein:
   the color imaging device comprises a CCD; and the apparatus further comprises a control unit for setting the brightness of the spectroscopic image within the predetermined range by controlling the charge storage time of the CCD.

7. The electronic endoscope apparatus according to claim 1, wherein the spectroscopic image generation circuit is a circuit that performs matrix operation on the RGB three color image signals using matrix data of the wavelength range forming a spectroscopic image to generate the spectroscopic image within the selected wavelength range.

8. An electronic endoscope apparatus, comprising:
a light source for irradiating white light on an observation target body;
a color imaging device for imaging the observation target image receiving the white light;
a first color conversion circuit for converting Y (luminance)/C (chrominance difference) signals outputted from the color imaging device to RGB three color image signals;
a spectroscopic image generation circuit for generating, from the RGB three color image signals, a spectroscopic image within a predetermined wavelength range, said spectroscopic image generation circuit performing a matrix operation using matrix data and the RGB three color image signals to generate the spectroscopic image which is described by spectroscopic three color image signals, and
wherein
said predetermined wavelength range is selected to visualize an anatomical characteristic of the observation target body, and
said predetermined wavelength range is a wavelength range which is narrower than the wavelength range of the observation target image imaged by the color imaging device, and
said matrix data comprises matrix parameters which correspond to said predetermined wavelength range;
a second color conversion circuit for converting the spectroscopic three color image signals representing the spectroscopic image to Y/C signals;
an amplifier circuit for gain adjustably amplifying the Y/C signals outputted from the color imaging device; and
a gain control circuit for controlling the gain of the amplifier circuit based on the luminance information provided by the Y/C signals outputted from the second color conversion circuit to set the brightness of the spectroscopic image described by the spectroscopic three color image signals, within a predetermined brightness range, for visualizing the spectroscopic image.

9. The electronic endoscope apparatus according to claim 8, further comprising:
a light amount regulation unit for regulating the amount of white light irradiated on the observation target body from the light source; and
a light amount control circuit for controlling the light amount regulation unit based on the luminance information provided by the Y/C signals outputted from the second color conversion circuit to set the brightness of the spectroscopic image within the predetermined range.

10. The electronic endoscope apparatus according to claim 9, wherein the light amount regulation unit comprises an aperture diaphragm disposed in the light path of the white light, and an aperture diaphragm drive section for regulating the opening of the aperture diaphragm.

11. The electronic endoscope apparatus according to claim 9, wherein the light amount regulation unit comprises a unit for controlling the drive current or drive voltage of the light source.

12. The electronic endoscope apparatus according to claim 9, wherein the light amount control circuit uses an average value of Y signals with respect to a single field of an image or a specific portion of the field as the luminance information.

13. The electronic endoscope apparatus according to claim 9, wherein the light amount control circuit uses a maximum value of Y signals with respect to a single field of an image or a specific portion of the field as the luminance information.

14. The electronic endoscope apparatus according to claim 8, wherein:
the color imaging device comprises a CCD; and
the apparatus further comprises a control unit for setting the brightness of the spectroscopic image within the predetermined range by controlling the charge storage time of the CCD.

15. The electronic endoscope apparatus according to claim 8, wherein the spectroscopic image generation circuit is a circuit that performs matrix operation on the RGB three color image signals using matrix data of the wavelength range forming a spectroscopic image to generate the spectroscopic image within the selected wavelength range.

16. An electronic endoscope apparatus as defined in claim 1, wherein:
the spectroscopic image generation circuit generates a spectroscopic image within a predetermined narrow wavelength range by administering matrix operations on the RGB three color signals output from the first color conversion circuit.

17. An electronic endoscope apparatus as defined in claim 8, wherein:
the spectroscopic image generation circuit generates a spectroscopic image within a predetermined narrow wavelength range by administering matrix operations on the RGB three color signals output from the first color conversion circuit.

* * * * *